United States Patent [19]
Pike

[11] Patent Number: 6,080,137
[45] Date of Patent: Jun. 27, 2000

[54] NEEDLE PROTECTOR

[75] Inventor: Kevin H. Pike, Ypsilanti, Mich.

[73] Assignee: Vadus, Inc., Amesbury, Mass.

[21] Appl. No.: 08/778,235

[22] Filed: Jan. 8, 1997

[51] Int. Cl.⁷ .................................................. A61M 5/00
[52] U.S. Cl. ........................ 604/263; 604/164; 604/177; 604/198
[58] Field of Search ................... 604/164, 165, 604/166, 171, 177, 178, 192, 198, 110, 263; 128/919

[56] References Cited

U.S. PATENT DOCUMENTS

| | | | |
|---|---|---|---|
| 4,211,741 | 7/1980 | Ostoich | 264/173 |
| 4,254,773 | 3/1981 | Waldbillig | 128/348 |
| 4,391,029 | 7/1983 | Czuba et al. | 29/450 |
| 4,424,833 | 1/1984 | Spector et al. | 137/849 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,683,916 | 8/1987 | Raines | 137/854 |
| 4,713,057 | 12/1987 | Huttner et al. | 604/164 |
| 4,728,322 | 3/1988 | Walker et al. | 604/165 |
| 4,781,703 | 11/1988 | Walker et al. | 604/264 |
| 4,801,295 | 1/1989 | Spencer | 604/198 |
| 4,832,696 | 5/1989 | Luther et al. | 604/164 |
| 4,846,805 | 7/1989 | Sitar | 604/165 |
| 4,850,961 | 7/1989 | Wanderer et al. | 604/53 |
| 4,883,699 | 11/1989 | Aniuk et al. | 428/36.9 |
| 4,917,669 | 4/1990 | Bonaldo | 604/164 |
| 4,944,728 | 7/1990 | Carrell et al. | 604/164 |
| 4,952,207 | 8/1990 | Lemieux | 604/164 |
| 5,000,736 | 3/1991 | Kaufhold, Jr. et al. | 604/110 |
| 5,000,740 | 3/1991 | Ducharme et al. | 604/162 |
| 5,013,304 | 5/1991 | Russell et al. | 604/167 |
| 5,019,049 | 5/1991 | Haining | 604/165 |
| 5,051,109 | 9/1991 | Simon | 604/263 |
| 5,088,985 | 2/1992 | Deras | 604/192 |
| 5,088,986 | 2/1992 | Nusbaum | 604/195 |
| 5,088,987 | 2/1992 | Noonan, Jr. | 604/195 |
| 5,088,988 | 2/1992 | Talonn et al. | 604/198 |
| 5,092,845 | 3/1992 | Chang | 604/164 |
| 5,092,853 | 3/1992 | Couvertier, II | 604/195 |
| 5,102,394 | 4/1992 | Lasaitis et al. | 604/164 |
| 5,108,374 | 4/1992 | Lemieux | 604/164 |
| 5,127,905 | 7/1992 | Lemieux | 604/164 |
| 5,135,504 | 8/1992 | McLees | 604/164 |
| 5,171,230 | 12/1992 | Eland et al. | 604/250 |
| 5,171,231 | 12/1992 | Heiliger | 604/263 |
| 5,176,650 | 1/1993 | Haining | 604/164 |
| 5,183,469 | 2/1993 | Capaccio | 604/192 |
| 5,188,597 | 2/1993 | Sweeney et al. | 604/110 |
| 5,188,607 | 2/1993 | Wu | 604/167 |
| 5,201,713 | 4/1993 | Rosetti | 604/165 |
| 5,215,525 | 6/1993 | Sturman | 604/164 |
| 5,215,527 | 6/1993 | Beck et al. | 604/164 |
| 5,215,528 | 6/1993 | Purdy et al. | 604/164 |
| 5,219,333 | 6/1993 | Sagstetter et al. | 604/110 |
| 5,222,947 | 6/1993 | D'Amico | 604/198 |
| 5,226,899 | 7/1993 | Lee et al. | 604/282 |
| 5,234,416 | 8/1993 | Macaulay et al. | 604/282 |

(List continued on next page.)

*Primary Examiner*—Wynn Wood Coggins
*Assistant Examiner*—Deborah Blyveis
*Attorney, Agent, or Firm*—Gardner, Carton & Douglas

[57] ABSTRACT

A needle protector having a body, a needle hub and a needle. The body has a first end and a second end. The body includes a plurality of side walls extending between the first and second ends in a geometric configuration. The side walls define an interior space. The side walls define a first slot and a second slot. The needle hub including a front end, a back end, a first side and a second side is positioned in the interior space of the body. The front end is adapted to receive a needle. The first and second sides each includes a handle device. The handle device extends through the slots to positions outside of the body. The needle is in communication with the front end of the needle hub. Movement of the handle devices causes corresponding movement of the needle. The needle can be retracted into the body and locked in position.

12 Claims, 5 Drawing Sheets

U.S. PATENT DOCUMENTS

| | | | |
|---|---|---|---|
| 5,240,537 | 8/1993 | Bodicky | 156/244.13 |
| 5,242,393 | 9/1993 | Brimhall et al. | 604/86 |
| 5,250,034 | 10/1993 | Appling et al. | 604/164 |
| 5,250,066 | 10/1993 | Lambert | 606/181 |
| 5,254,107 | 10/1993 | Soltesz | 604/282 |
| 5,261,885 | 11/1993 | Lui | 604/247 |
| 5,267,971 | 12/1993 | Brimhall | 604/177 |
| 5,267,979 | 12/1993 | Appling et al. | 604/247 |
| 5,273,543 | 12/1993 | Bell et al. | 604/110 |
| 5,279,590 | 1/1994 | Sinko et al. | 604/263 |
| 5,279,591 | 1/1994 | Simon | 604/263 |
| 5,300,048 | 4/1994 | Drewes, Jr. et al. | 604/280 |
| 5,304,136 | 4/1994 | Erskine et al. | 604/110 |
| 5,304,140 | 4/1994 | Kugo et al. | 604/281 |
| 5,304,144 | 4/1994 | Brimhall | 604/177 |
| 5,304,149 | 4/1994 | Morigi | 604/192 |
| 5,304,155 | 4/1994 | Lui | 604/247 |
| 5,306,253 | 4/1994 | Brimhall | 604/165 |
| 5,308,330 | 5/1994 | Grimard | 604/110 |
| 5,312,361 | 5/1994 | Zadini et al. | 604/165 |
| 5,312,371 | 5/1994 | Dombrowski et al. | 604/198 |
| 5,316,706 | 5/1994 | Muni et al. | 264/25 |
| 5,318,547 | 6/1994 | Altschuler | 604/198 |
| 5,328,473 | 7/1994 | Fayngold et al. | 604/110 |
| 5,334,144 | 8/1994 | Alchas et al. | 604/68 |
| 5,338,310 | 8/1994 | Lewandowski | 604/192 |
| 5,342,309 | 8/1994 | Hausser | 604/110 |
| 5,344,404 | 9/1994 | Benson | 604/110 |
| 5,344,408 | 9/1994 | Partika | 604/192 |
| 5,356,390 | 10/1994 | Erskine | 604/164 |
| 5,370,624 | 12/1994 | Edwards et al. | 604/169 |
| 5,376,073 | 12/1994 | Graves et al. | 604/86 |
| 5,380,298 | 1/1995 | Zabetakis et al. | 604/265 |
| 5,380,307 | 1/1995 | Chee et al. | 604/264 |
| 5,385,554 | 1/1995 | Brimhall | 604/168 |
| 5,385,555 | 1/1995 | Hausser | 604/110 |
| 5,395,341 | 3/1995 | Slater | 604/164 |
| 5,397,512 | 3/1995 | Sloane, Jr. et al. | 264/25 |
| 5,405,323 | 4/1995 | Rogers et al. | 604/53 |
| 5,405,326 | 4/1995 | Haber et al. | 604/110 |
| 5,407,431 | 4/1995 | Botich et al. | 604/110 |
| 5,409,461 | 4/1995 | Steinman | 604/110 |
| 5,409,463 | 4/1995 | Thomas et al. | 604/167 |
| 5,409,644 | 4/1995 | Martin et al. | 264/25 |
| 5,411,486 | 5/1995 | Zadini et al. | 604/198 |
| 5,415,184 | 5/1995 | Peck | 128/880 |
| 5,417,668 | 5/1995 | Setzer et al. | 604/263 |
| 5,419,766 | 5/1995 | Chang et al. | 604/110 |
| 5,419,777 | 5/1995 | Hofling | 604/264 |
| 5,423,758 | 6/1995 | Shaw | 604/110 |
| 5,423,766 | 6/1995 | Di Cesare | 604/192 |
| 5,423,773 | 6/1995 | Jimenez | 604/282 |
| 5,425,712 | 6/1995 | Goodin | 604/96 |
| 5,425,735 | 6/1995 | Rosen et al. | 606/128 |
| 5,425,903 | 6/1995 | Sloane, Jr. et al. | 264/22 |
| 5,429,613 | 7/1995 | D'Amico | 604/198 |
| 5,429,617 | 7/1995 | Hammersmark et al. | 604/264 |
| 5,435,314 | 7/1995 | Dias | 128/662.06 |
| 5,437,648 | 8/1995 | Graves et al. | 604/263 |
| 5,441,489 | 8/1995 | Utsumi et al. | 604/280 |
| 5,443,457 | 8/1995 | Ginn et al. | 604/280 |
| 5,445,619 | 8/1995 | Burns | 604/192 |
| 5,445,624 | 8/1995 | Jimenez | 604/280 |
| 5,446,230 | 8/1995 | Travers et al. | 585/748 |
| 5,447,501 | 9/1995 | Karlsson et al. | 604/198 |
| 5,447,503 | 9/1995 | Miller | 604/280 |
| 5,447,724 | 9/1995 | Helmus et al. | 424/426 |
| 5,449,349 | 9/1995 | Sallee et al. | 604/180 |
| 5,453,095 | 9/1995 | Davila et al. | 604/167 |
| 5,453,099 | 9/1995 | Lee et al. | 604/282 |
| 5,456,668 | 10/1995 | Ogle, II | 604/110 |
| 5,456,674 | 10/1995 | Bos et al. | 604/280 |
| 5,458,658 | 10/1995 | Sircom | 604/192 |
| 5,462,533 | 10/1995 | Daugherty | 604/164 |
| 5,464,398 | 11/1995 | Haindl | 604/280 |
| 5,464,399 | 11/1995 | Boettger | 604/283 |
| 5,472,430 | 12/1995 | Vaillancourt et al. | 604/198 |
| 5,474,539 | 12/1995 | Costa et al. | 604/164 |
| 5,478,313 | 12/1995 | White | 604/110 |
| 5,478,328 | 12/1995 | Silverman et al. | 604/272 |
| 5,487,732 | 1/1996 | Jeffrey | 604/110 |
| 5,501,672 | 3/1996 | Firth et al. | 604/177 |
| 5,520,654 | 5/1996 | Wahlberg | 604/164 |
| 5,531,701 | 7/1996 | Luther | 604/165 |
| 5,562,631 | 10/1996 | Bogert | 604/164 |

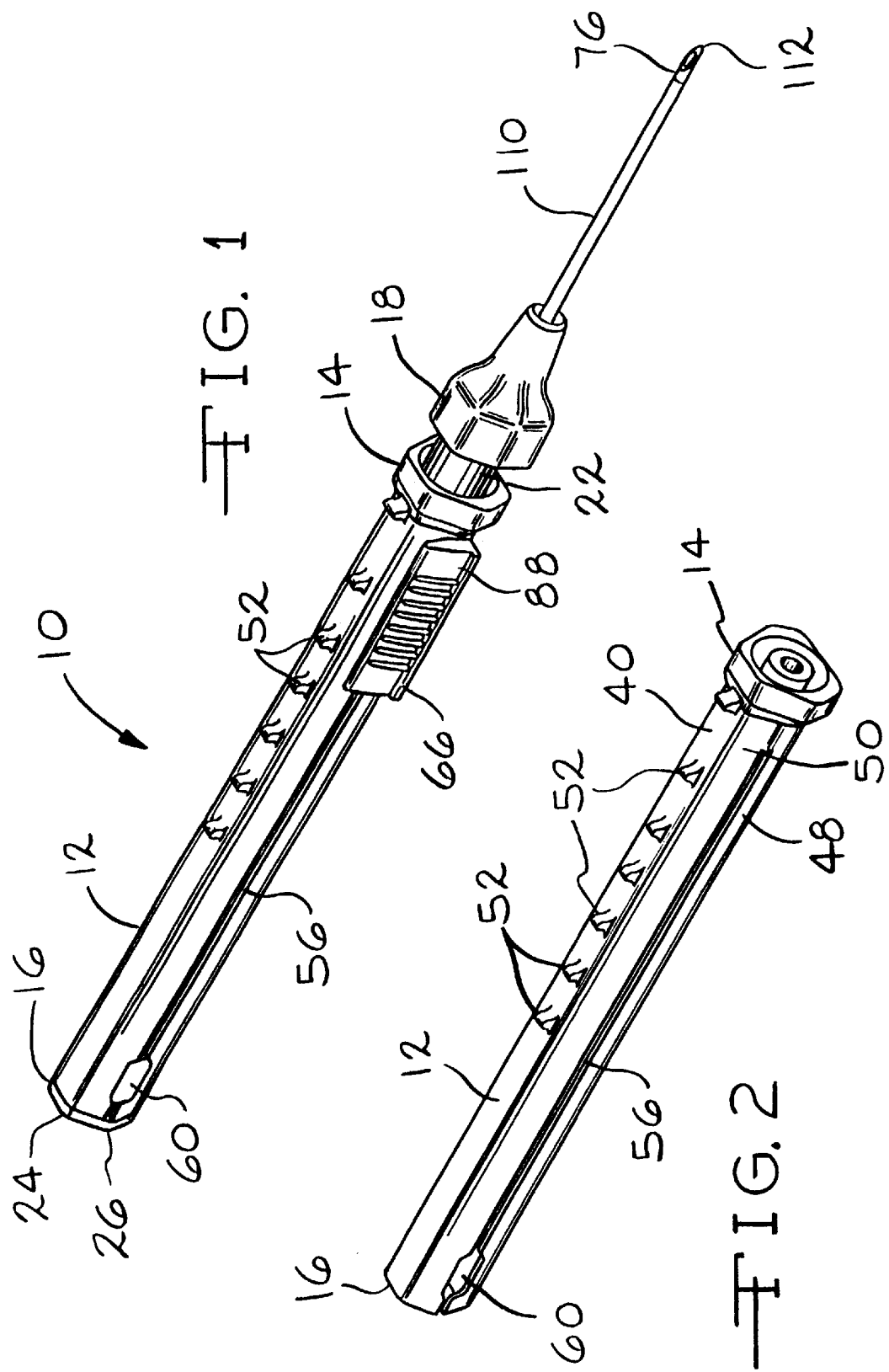

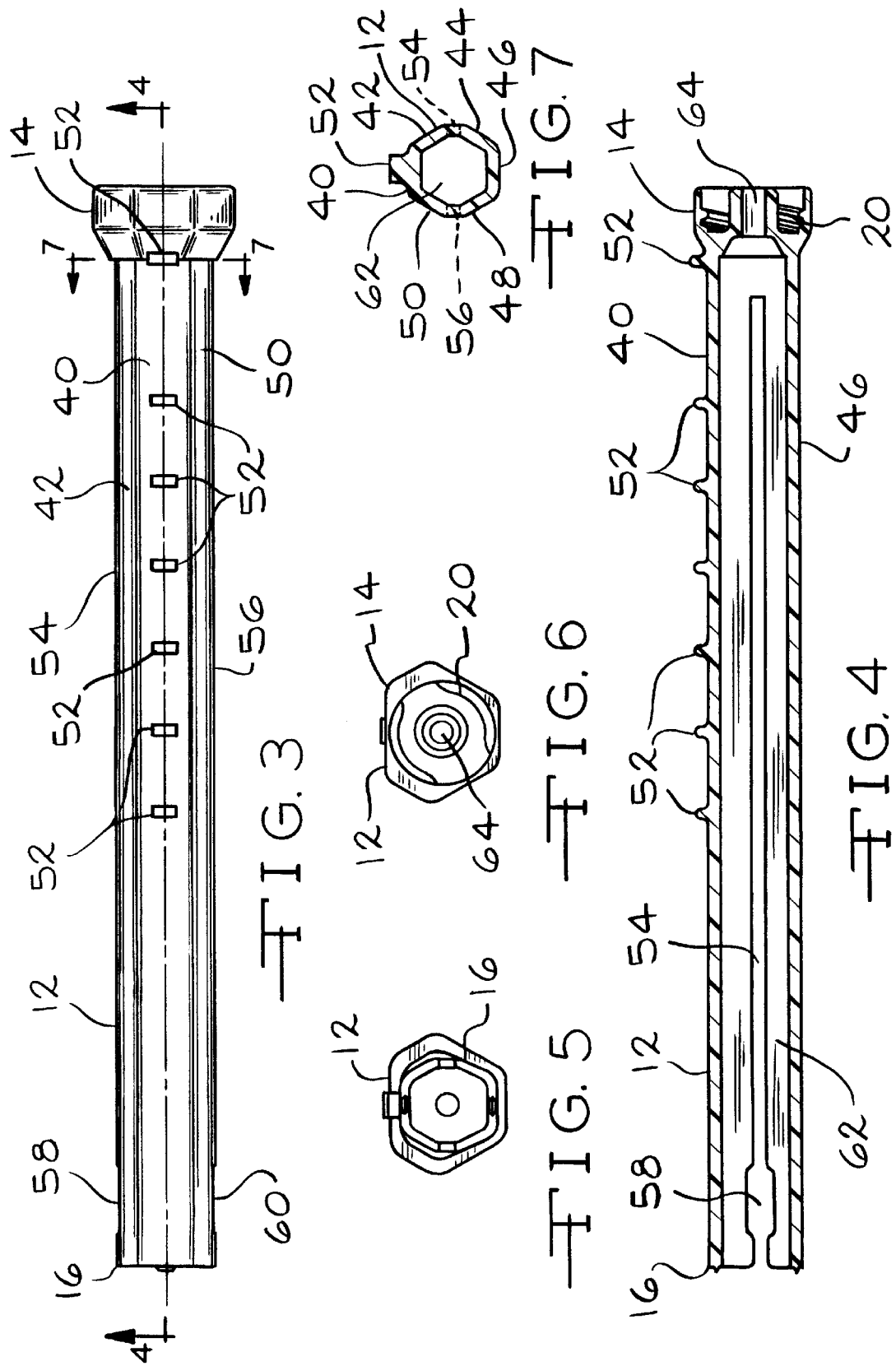

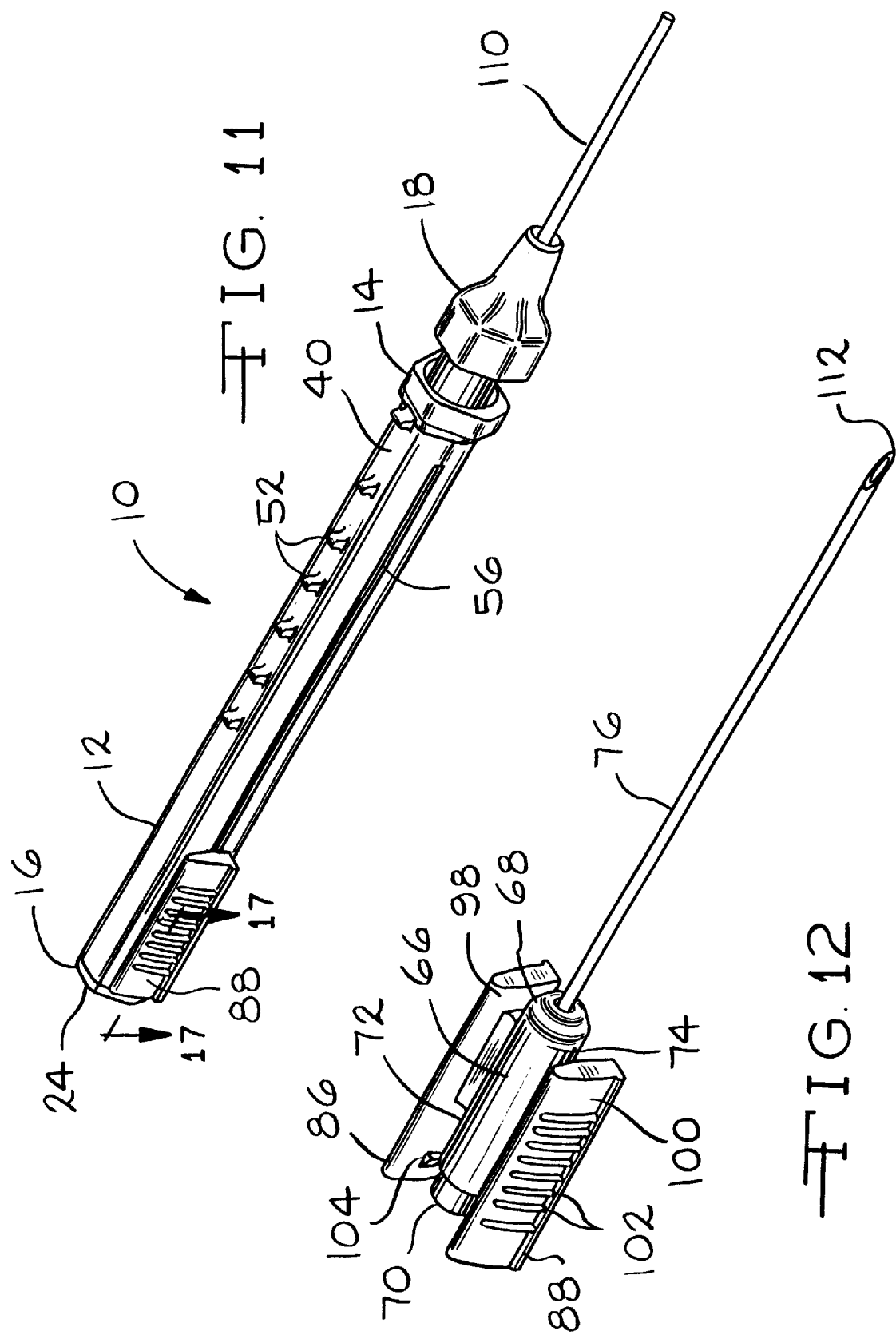

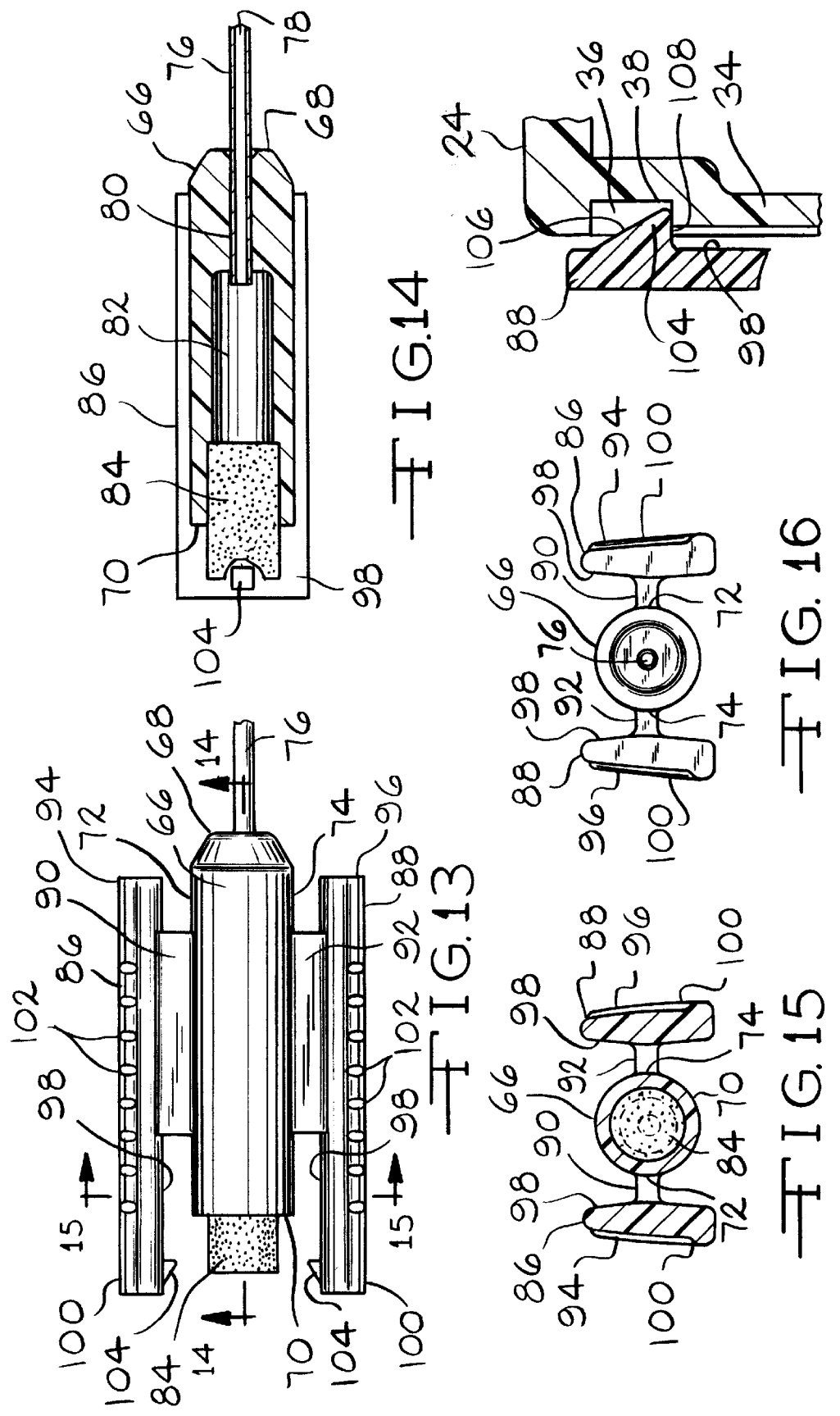

NEEDLE PROTECTOR

BACKGROUND OF THE INVENTION

The present invention relates to a needle protector. More specifically, the invention is directed to a needle protector having a body, a needle hub and a needle. The needle is mounted on the needle hub. When the needle hub is moved along body, the needle is retracted into the body where it is locked into position.

It has been determined that certain viruses such as the hepatitis B virus can be transmitted from one person to another by accidental "needle-pokes". This type of accident can happen during medical procedures. An example of such a procedure is the insertion of a catheter into a blood vessel of a patient with a needle. After the catheter has been inserted in the blood vessel, the needle is removed from the catheter at which time the pointed end of the needle can be accidentally poked into the person handling the needle or someone in the vicinity of the needle. The residual blood on the needle can be inserted in the person poked by the needle thereby transmitting a virus in the blood.

It has been found that there is a need for a needle protector in which the needle can be easily handled during insertion in a patient and then retracted into the body of the needle protector and locked into place so that the pointed end of the needle cannot come into contact with another person. The present invention satisfies this need.

SUMMARY OF THE INVENTION

The present invention is directed to a needle protector including a body, a needle hub and a needle. The body has a first end and a second end. The body includes a plurality of side walls extending between the first and second ends in a geometric configuration, such a hexagon. The side walls define an interior space. The side walls define at least two slots.

The needle hub having a front end, a back end, a first side and a second side is positioned in the interior space of the body. The front end is adapted to receive a needle. The first and second sides each includes a handle. The handles extend through the slots of the body to positions outside of the body.

The needle is in communication with the front end of the needle hub. Movement of the handles of the needle hub causes corresponding movement of the needle. Therefore, when the handles are moved from the first end of the body to the second end of the body along the slots of the body, the needle moves from the exterior of the body into the interior space defined by the body. Accordingly, the needle is fully contained in the body thereby preventing accidental needle-pokes.

It is the primary object of the present invention to provide a needle protector including a body having a unique geometric configuration that allows the needle protector to be accurately and easily handled.

It is an important object of the present invention to provide a needle protector including a needle hub having at least two wings to provide for accurate manipulation of the needle hub.

It is another important object of the present invention to provide a needle protector defining an interior space for receiving a needle to contain the needle within the body of the needle protector.

It is another important object of the present invention to provide a needle protector in which each of the wings includes locking members for locking the needle hub in proper position once the needle has been retracted into the body.

Other objects and advantages of the present invention will become apparent to those skilled in the art upon a review the following detailed description of the preferred embodiment and the accompanying drawings.

BRIEF DESCRIPTION OF THE DRAWINGS

FIG. 1 is a perspective view of a needle protector according to the present invention attached to a catheter hub;

FIG. 2 is a perspective view of the body of the present needle protector;

FIG. 3 is a top view of the body of the present needle protector;

FIG. 4 is a cross-sectional view taken along line 4—4 of FIG. 3;

FIG. 5 is an elevational view of the second end of the body of the present needle protector;

FIG. 6 is an elevational view of the first end of the body of the present needle protector;

FIG. 7 is a cross-sectional view taken along line 7—7 of FIG. 3;

FIG. 11 is a view similar to the view of FIG. 1 in which the needle hub according to the present invention has been moved from the first end of the body to the second end of the body;

FIG. 12 is a perspective view of the needle hub and needle according to the present invention;

FIG. 13 is a top view of the needle hub according to the present invention;

FIG. 14 is a cross-sectional view taken along line 14—14 of FIG. 13;

FIG. 15 is a cross-sectional view taken along line 15—15 of FIG. 13;

FIG. 16 is an elevational view of the back end of the needle hub; and

FIG. 17 is a cross-sectional view taken along line 17—17 of FIG. 11.

DETAILED DESCRIPTION OF THE PREFERRED EMBODIMENT

Figure 9:
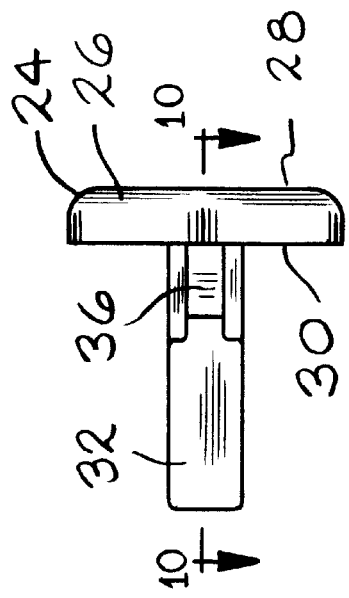
FIG. 9 is a side elevational view of the end cap shown in FIG. 8.

The preferred embodiment and best mode of the present invention will now be described in detail with reference being made to the drawings. The needle protector of the present invention is indicated generally in the drawings by the reference number "10".

Referring to FIGS. 1–7, the needle protector 10 includes a body 12 having a first end 14 and a second end 16. As shown in FIGS. 1, 2, 4 and 6, the first end 14 is adapted to receive a catheter hub 18. For example, the first end 14 includes a plurality of threads 20, as shown in FIG. 4, for receiving mating threads (not shown) positioned on the connection end 22 of the catheter hub 18. It should be understood that the first end 14 of the needle protector 10 can be adapted to receive a variety of devices depending on the application. For the purpose of explanation, the catheter hub 18 shown in the present drawings will be used in conjunction with the needle protector 10.

Figure 10:
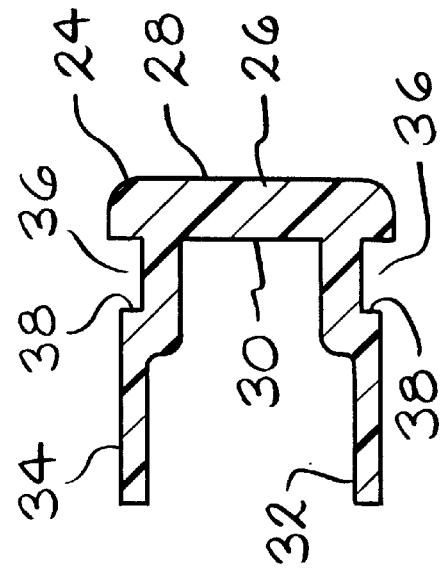
FIG. 10 is a cross-sectional view taken along line 10—10 of FIG. 9.
Figure 8:
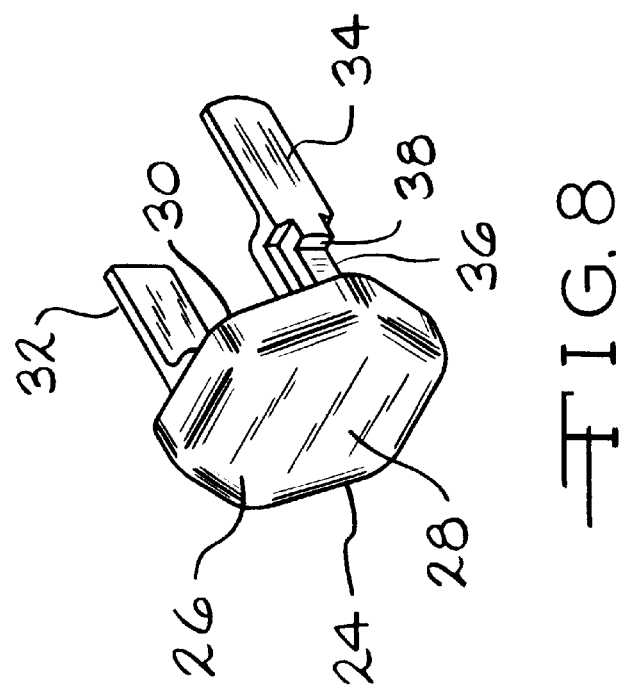
FIG. 8 is a perspective view of the end cap according to the present invention.

As shown in FIGS. 1, 4, 5 and 8–10, the second end 16 of the body 12 can be adapted to receive an end cap 24. As shown in FIGS. 8–10, the cap 24 includes a head 26 having an exterior surface 28 and an interior surface 30. A first leg 32 and a second leg 34 extend outwardly from the interior surface 30 of the head 26. As shown in FIG. 10, each of the first and second legs 32 and 34 includes a locking recess 36 having a locking surface 38. The first and second legs 32 and 34 are inserted in the second end 16 of the body 12 to attach the cap 24 to the body.

Referring to FIGS. 2, 3, 4 and 7, the body 12 includes a plurality of side walls extending between the first end 14 and the second end 16 in a geometric configuration. In the preferred embodiment, as shown in FIG. 7, the body 12 includes a first side wall 40, a second side wall 42, a third side wall 44, a fourth side wall 46, a fifth side wall 48 and a sixth side wall 50. The side walls 40–50, are arranged to form a hexagonal configuration. It should be understood that the number of side walls of the body 12 can be changed to form various polygonal configurations, with a hexagonal configuration being preferred. As described below, the hexagonal configuration allows the needle protector 10 to be easily handled during use. For example, the fourth side wall 46 provides a flat, smooth surface for contact with, for example, the skin of a patient. The first side wall 40 provides a surface upon which, for example, a thumb of a person using the needle protector 10 can rest during handling. As shown in FIGS. 2, 3 and 4, a plurality of spaced upwardly extending projections 52 are positioned on the first side wall 40. The projections 52 may be engaged by the thumb to more accurately and easily handle the needle protector 10.

Referring to FIGS. 2, 4 and 7, the side walls of the body 12 define at least two slots. In the preferred embodiment, the second and third side walls 42 and 44 define a first slot 54, and the fifth and sixth side walls 48 and 50 define a second slot 56. The first and second slots 54 and 56 extend longitudinally between the first end 14 and the second end 16 of the body 12 in an opposed relationship to one another. As shown in FIGS. 2–4, the first and second slots 54 and 56 define first and second locking portions 58 and 60, respectively, adjacent the second end 16 of the body 12 in opposed relationship to one another. The first and second locking portions 58 and 60 are positioned adjacent the locking recesses 36 of the first and second legs 32 and 34 of the end cap 24.

Referring to FIGS. 4 and 7, the side walls 40–50 define an interior space 62 extending between the first and second ends 14 and 16 of the body 12. As shown in FIG. 4, a needle opening 64 is defined by the body 12 at the first end 14. The needle opening 64 extends from the exterior of the body 12 to the interior space 62.

Referring to FIGS. 11–17, the needle protector 10 includes a needle hub 66 having a front end 68, a back end 70, a first side 72 and second side 74. The needle hub 66 is movably positioned in the interior space 62 of the body 12. As shown in FIG. 14, the front end 68 of the needle hub 66 is adapted to receive a needle 76 having a needle fluid passageway 78. The front end 68 includes a front end opening 80 for receiving the needle 76. The needle hub 66 defines a hub fluid passageway 82 extending between the front and back ends 68 and 70. The needle 76 is positioned in the front end opening 80 so that the needle fluid passageway 78 is in communication with the hub fluid passageway 82. As shown in FIGS. 13 and 14, the back end 70 of the needle hub 66 is adapted to receive absorbent material 84. The absorbent material 84 absorbs any fluid, such as blood, contained in the hub fluid passageway 82.

Referring to FIGS. 13, 15 and 16, the first and second sides 72 and 74 of the needle 66 include first and second handles 86 and 88, respectively. The first and second handles 86 and 88 include first and second wings 90 and 92, respectively. The first and second wings 90 and 92 extend from the needle hub 66 through the first and second slots 54 and 56, respectively, to the exterior of the body 12.

Still referring to FIGS. 13, 15 and 16, the first and second handles 86 and 88 include first and second handle members 94 and 96, respectively, attached to the first and second wings 90 and 92, respectively. Each of the first and second handle members 94 and 96 includes an interior surface 98 and an exterior surface 100. As shown in FIG. 13, each exterior surface 100 includes a plurality of spaced grips 102. The grips 102 allow the first and second handles 86 and 88 to be firmly gripped during actuation of the needle hub 66.

Referring to FIGS. 10, 13 and 17, the first and second handle members 94 and 96 each includes a locking projection 104 extending inwardly from the interior surface 98. Each locking projection 104 includes a ramp surface 106 and a locking surface 108. As shown in FIG. 17, the locking projections 104 are received by the locking recesses 36 of the first and second legs 32 and 34. The locking surfaces 108 of the locking projections 104 engage the recess surfaces 38 of the locking recesses 36 to lock the needle hub 66 to the second end 16 of the body 12.

Referring to FIGS. 1, 11, 14 and 17, the operation and intended use of the needle protector 10 will now be described. As shown in FIG. 1, the catheter hub 18 includes a catheter 110. The needle hub 66 is positioned adjacent the first end 14 of the body 12. When the needle hub 66 is so positioned, the needle 76, which includes a pointed end 112, extends through the catheter hub 18 and the catheter 110. When the catheter 110 is to be inserted, for example, in the blood vessel of a patient (not shown), the needle protector 10 is moved to the site of the blood vessel. The user of the needle protector 10 grips the body 12 and places his or her index finger on the first side wall 40. The finger engages the projections 52 so that the body 12 can be accurately positioned with respect to the blood vessel. Fourth side wall 46 is positioned on the surface of the skin of the patient adjacent the blood vessel. It has been found that the smooth, flat surface provided by the fourth side wall 46 aids in the positioning of the needle protector 10 with respect to the blood vessel. When the pointed end 112 of the needle 76 is properly positioned, the user of the needle protector 10 pushes the pointed end of the needle 112 into the blood vessel. Blood from the blood vessel "flashes" or enters the needle fluid passageway 78 and proceeds to the hub fluid passageway 82. The absorbent material 74 absorbs the blood to prevent leakage from the needle hub 66. Insertion of the needle 76 into the blood vessel results in the insertion of the catheter 110 into the blood vessel.

Referring to FIGS. 11 and 17, after the catheter 110 has been inserted, the user of the needle protector 10 uses his or her thumb and forefinger to engage the first and second handles 86 and 88 of the needle hub 66. The grips 102 prevent slippage by the user. The user pulls back on the first and second handles 86 and 88 thereby causing the needle hub 66 to move from the first end 14 to the second end 16 of the body 12. The first and second wings 90 and 92 travel along the first and second slots 54 and 56, respectively, to guide the needle hub 66 along its predetermined path. The first and second wings 90 and 92 maintain the needle hub 66 in proper axial alignment with respect to the body 12. Movement of the needle hub 66 causes corresponding movement of the needle 76. As the needle hub 66 moves toward the second end 16 the needle 76 passes through the needle opening 64 into the interior space 62 of the body 12.

When the needle hub 66 is positioned adjacent the second end 16 of the body 12, the needle 76 is fully contained in the interior space 62. As shown in FIG. 17, the locking projections 104 are received by the locking recesses of the cap 24 to prevent forward movement of the needle hub 66. The engagement of the locking surface 108 to the recess surface 38 provides a positive lock so that the needle 76 cannot exit through the needle opening 64.

After the needle 76 has been locked in place, the user of the needle protector disengages the needle protector from the catheter hub 18. The catheter hub 18 can then be used as intended.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A needle protector, comprising
  a body having a first end and a second end and an end cap attached to said second end, said body including a plurality of side walls extending between said first and second ends in a geometric configuration, said side walls defining an interior space and a first slot and a second slot, said slots each having a single locking portion adjacent to said second end;
  a needle hub having a front end, a back end, a first side and a second side being positioned in said interior space, said front end being adapted to receive a needle, said first and second sides each including a handle, said handle extending through said slots to positions outside of said body and consisting of a wing and a handle member, said handle member having an exterior surface and an interior surface and at least one locking projection on said interior surface; and
  a needle in communication with said front end of said needle hub, whereby movement of said needle hub from said front end to said back end results in corresponding movement of said needle into said body until said locking projection of said handle member irreversibly engages said locking portion, locking said needle in a fully retracted position with said handle at least partly covered by said end cap.

2. The invention of claim 1, wherein said first end is adapted to receive a catheter hub.

3. The invention of claim 1, wherein one of said side walls includes a plurality of spaced projections.

4. The invention of claim 1, wherein said geometric configuration is a polygon.

5. The invention of claim 4, wherein said polygon is a hexagon.

6. The invention of claim 1, wherein said slots are opposed in relation to one another.

7. The invention of claim 1, wherein said needle hub includes a fluid passageway extending between said front and back ends.

8. The invention of claim 7, wherein said back end includes absorbent means.

9. The invention of claim 7, wherein said needle defines a needle passageway in communication with said fluid passageway of said needle hub.

10. The invention of claim 1, wherein said handle member includes an interior surface, and an exterior surface including a plurality of spaced grips.

11. The invention of claim 10, wherein said end cap includes a first and a second leg, each of said legs defining a locking portion for receiving said locking projection.

12. A needle protector, comprising:
  a body having a first end, a second end having a cap, and at least one handle, with said body defining a plurality of openings adjacent said second end;
  a needle hub including a plurality of locking means, said locking means being received by said openings to irreversibly lock said needle hub into adjacent said second end and wherein said handle is at least partly covered by and locked into said cap.

* * * * *